United States Patent
Ibert et al.

(10) Patent No.: US 9,334,287 B2
(45) Date of Patent: May 10, 2016

(54) HIGH-FLUIDITY NON-CAKING DIANHYDROHEXITOL PELLETS

(71) Applicant: ROQUETTE FRERES

(72) Inventors: Mathias Ibert, La Chapelle D'armentieres (FR); Jerome Saint Pol, Lapugnoy (FR); Herve Wyart, Cuinchy (FR)

(73) Assignee: ROQUETTE FRERES, Lestrem (FR)

( * ) Notice: Subject to any disclaimer, the term of this patent is extended or adjusted under 35 U.S.C. 154(b) by 0 days.

(21) Appl. No.: 14/834,603

(22) Filed: Aug. 25, 2015

(65) Prior Publication Data

US 2015/0361086 A1 Dec. 17, 2015

Related U.S. Application Data

(63) Continuation of application No. 13/824,613, filed as application No. PCT/FR2011/052289 on Sep. 30, 2011, now Pat. No. 9,163,031.

(30) Foreign Application Priority Data

Sep. 30, 2010 (FR) ..................................... 10 57949

(51) Int. Cl.
*C07D 493/04* (2006.01)
*B01J 2/26* (2006.01)
*B01J 2/30* (2006.01)

(52) U.S. Cl.
CPC .................. *C07D 493/04* (2013.01); *B01J 2/26* (2013.01); *B01J 2/30* (2013.01); *Y10T 428/2982* (2015.01)

(58) Field of Classification Search
CPC ....................................................... C07D 493/04
USPC ........................................................... 428/402
See application file for complete search history.

(56) References Cited

U.S. PATENT DOCUMENTS

| | | |
|---|---|---|
| 4,435,603 A | 3/1984 | Cornils et al. |
| 8,283,009 B2 | 10/2012 | Fuertes et al. |
| 2003/0097028 A1 | 5/2003 | Fuertes |
| 2004/0110969 A1 | 6/2004 | Fleche et al. |

FOREIGN PATENT DOCUMENTS

| | | |
|---|---|---|
| EP | 1287000 | 3/2003 |
| EP | 1446373 | 8/2004 |
| FR | 2477902 | 9/1981 |
| FR | 2919587 | 2/2009 |
| JP | 2006117649 | 5/2006 |
| WO | 03043959 | 5/2003 |
| WO | 2009010673 | 1/2009 |

OTHER PUBLICATIONS

International Search Report dated Dec. 5, 2011, corresponding to PCT/FR2011/052289.

*Primary Examiner* — Taofiq A Solola
(74) *Attorney, Agent, or Firm* — Young & Thompson

(57) ABSTRACT

Dianhydrohexitol pellets, whose fluidity is preserved even after lengthy storage, include between 90% and 100%, preferably between 95% and 100%, and more preferentially between 97% and 100% of dianhydrohexitols by weight, on a dry weight basis, and have the particularity of not being subject to caking. A process for preparing the dianhydrohexitol pellets is also described.

13 Claims, No Drawings

HIGH-FLUIDITY NON-CAKING DIANHYDROHEXITOL PELLETS

FIELD OF THE INVENTION

The present invention relates to dianhydrohexitol pellets, the fluidity of which is retained even after long term storage. These dianhydrohexitol pellets thus exhibit the distinguishing feature of not being subject to caking.

PRIOR ART

Dianhydrohexitols (1,4:3,6-dianhydrohexitols), also known as isohexides, are products of the internal dehydration of hydrogenated $C_6$ sugars (hexitols), such as sorbitol, mannitol and iditol. In the present patent application, the term "dianhydrohexitols" encompasses isosorbide (1,4:3,6-dianhydrosorbitol), isomannide (1,4:3,6-dianhydromannitol), isoidide (1,4:3,6-dianhydroiditol) and the mixtures of at least two of these products.

The industrial applications of dianhydrohexitols are currently experiencing vigorous growth, in particular in the pharmaceutical field, in that of chemical synthesis intermediates and that of plastics.

For the majority of these applications, it is generally necessary to have available compositions which are as pure as possible, in particular having a dianhydrohexitol content at least equal to 98.5% by weight, preferably at least equal to 99.5% by weight, of said compositions on a dry basis.

Dianhydrohexitols, in particular isosorbide, are highly hygroscopic and chemically rather unstable products and are consequently greatly subject to caking.

The Applicant Company has in particular observed that the storage of dianhydrohexitols manufactured according to known processes led, under certain humidity and temperature conditions, to significant caking and chemical decomposition.

The dianhydrohexitol compositions thus caked during storage raise a good number of problems. This is because the caking not only causes serious handling difficulties during operations such as the transfer thereof, the unpacking thereof, the milling thereof, the redissolution thereof, and the like, but it also has a major impact on the output of these operations.

A number of solutions have been proposed in order to overcome these difficulties:
- to add anticaking agents to the dianhydrohexitol composition,
- to prepare a specific external packaging material such that it prevents the uptake of water by the composition and consequently the caking of said composition.

Thus, in the more general field of the polyols, the patent JP No. 74 88 183 discloses the addition of esters of organic acids or of acetals as anticaking agents. According to this patent, the addition of 0.005% by weight of butyl cellulose acetate makes it possible for neopentyl glycol not to exhibit caking for 30 days under a pressure of 0.23 bar after the forming thereof.

Another method for preventing polyols from caking has also been described in the patent FR No. 2 477 902. It has thus been proposed to add from 0.005% to 0.25% by weight of tertiary amines which comprise at least two identical organic substituents in order to prevent the caking of polyols.

However, the addition of anticaking agents is not generally selected by specialists in the specific field of dianhydrohexitol compositions, in particular because:
- the introduction of impurities into said compositions may harm their properties and thus their commercial value,
- regulatory constraints forbid the use of such additives in some applications.

With regard to the use of a method for packaging the dianhydrohexitol compositions, this second technical solution has not to date given entirely satisfactory results.

Among these packaging methods, the patent application JP 2006-117649 discloses the use of a packaging material of film type for packaging isosorbide with the aim of protecting the latter from water absorption, of keeping it in the fluid powder form and of preventing formation of aggregates. The packaging film is defined as being a multilayer film based on plastics and aluminum.

The Applicant Company has itself prepared a packaging based on thermoplastic polymer for packaging dianhydrohexitols. Said packaging, disclosed in the patent application FR No. 2 919 587, is intended for both solid and liquid dianhydrohexitol compositions. The solid forms concerned may, for example, be cooled and solidified distillates or may be crystals, it being possible for all of these products to be provided in particular in the form of a powder or flakes. However, said packaging has given very good results in terms of prevention of chemical decomposition of dianhydrohexitol compositions during storage but has not made it possible to lastingly prevent the caking of said compositions.

The aim of the present invention is thus to provide dianhydrohexitol compositions, the fluidity of which is preserved even after storage of several hundred stacked kilograms of product for long periods of time.

Another specific aim of the present invention is also to provide dianhydrohexitol compositions which can easily flow, which are easy to meter out by volume and which leave no or virtually no residues in the empty packaging after use.

A specific aim of the present invention is to provide compositions which form little or no dust.

Another aim of the present invention is to provide compositions which employ very small amounts of anticaking agent and which advantageously do not employ any of it at all.

Another aim of the present invention is to provide compositions with an extremely high content of dianhydrohexitols, in particular of isosorbide, i.e. comprising between 90% and 100% by weight, preferably between 95% and 100% by weight and more preferably still between 97% and 100% by weight on a dry basis of dianhydrohexitols.

Another aim of the present invention is to provide dianhydrohexitol compositions which can exhibit a relatively high residual moisture content, for example of the order of from 0.2% to 0.5% by weight of said compositions, and which nevertheless exhibit a low propensity to cake.

Yet another aim of the present invention is to provide dianhydrohexitol compositions capable of being rapidly dissolved or melted.

SUMMARY OF THE INVENTION

A subject matter of the present invention is dianhydrohexitol pellets comprising between 90% and 100% by weight, preferably between 95% and 100% by weight and more preferably between 97% and 100% by weight on a dry basis of the composition of said dianhydrohexitol pellets. The dianhydrohexitol pellets according to the invention comprise less than 2% by weight of anticaking agent, preferably less than 0.5% by weight, more preferably still less than 0.01% by weight and more preferably still less than 0.001% by weight on a dry basis of the composition of said dianhydrohexitol pellets. Advantageously, the pellets according to the invention are devoid of any anticaking agent and are nevertheless not very subject to caking.

Another subject matter of the invention is a process for the preparation of said dianhydrohexitol pellets.

DETAILED DESCRIPTION

A subject matter of the present invention is dianhydrohexitol pellets comprising between 90% and 100% by weight, preferably between 95% and 100% by weight and more preferably between 97% and 100% by weight (dry/dry) of the composition of said dianhydrohexitol pellets. More preferably still, the pellets according to the invention exhibit a dianhydrohexitol content of greater than or equal to 98.5% by weight, preferably of greater than or equal to 99.5% by weight, (dry/dry) of the composition of said dianhydrohexitol pellets. The remainder to 100% by weight on a dry basis of the composition of said dianhydrohexitol pellets can be composed of hexitols, monoanhydrohexitols, stabilizing agents, such as those mentioned in the patent EP 1 446 373, anticaking agents, and various impurities and coproducts, such as those mentioned in the patent EP 1 287 000 (section [0008]) and related to the process for the production of the dianhydrohexitols, in particular to the dehydration stage of said process.

The pellets according to the invention in addition do not comprise much anticaking agent or do not comprise anticaking agent and are nevertheless not very subject to caking.

Another subject matter of the invention is a process for the preparation of said dianhydrohexitol pellets.

In the present patent application, the term "pellet" is understood to mean a compact three-dimensional product obtained by "pelleting". Thus, the term "pellet" comprises the terms tablet, pebble, granule, bar, bead and/or any other shape obtained by "pelleting". Said pellet can exhibit flat or rounded and concave or convex upper and lower faces. Said pellet can without distinction be of round, oval, square, rectangular, octagonal, polygonal, and the like, general shape. Preferably, the pellet according to the invention is dome-shaped, that is to say that it has a flat face and a convex face, the edges between the two faces being more or less softened.

In the present patent application, the term "pelleting" is understood to mean a process combining a stage of dropping drops with a stage of cooling said drop, said process thus making it possible to produce pellets with stable and uniform shapes which are substantially devoid of particles having a fine particle size. In the present patent application, the term "drop" is understood to mean any defined amount of molten product. Thus, the pellets according to the invention are solidified directly from molten dianhydrohexitols, thus eliminating energy and equipment costs associated with subsequent stages of milling or crushing or with any other stage of the same type.

The pellets according to the invention can be obtained by employing different types of pelletizers, such as disk pelletizers, belt pelletizers, and the like. In particular, the pelleting according to the invention can be carried out according to the pelleting processes described in the patent application WO 2009/010673.

Prior to the pelleting process, the dianhydrohexitol composition is maintained in the molten state in a feed vessel. Dianhydrohexitol "melt" is then referred to. To do this, the dianhydrohexitol(s) is/are advantageously maintained at a temperature greater than or equal to its/their melting point, in particular, for isosorbide, at a temperature greater than or equal to 63±2° C. The dianhydrohexitol composition can result from a distillation of a crude reaction mixture, from a melting of a product purified by crystallization in the molten phase or in an aqueous or organic solvent, or from a concentrating to dryness of a dianhydrohexitol solution purified according to the patent EP 1 287 000.

Preferably, the melt is introduced into the pelleting unit via a heated pipeline and a constant-delivery pump. The adjustable pump makes it possible to feed the pelletizer at the required pressure.

The first stage of the pelleting process consists of the production of dianhydrohexitol drops from a melt. According to a preferred form of the invention, the melt arrives at a feed/metering unit where it is converted into pellets, the particle size and the amount of which are determined by the diameter and the number of holes or nozzles selected. It is injected into one or more drop generators, for example by excess pressure, which convert the continuous product flow into uniform drops of predetermined diameter.

The stage of production of dianhydrohexitol drops is followed by a stage of cooling of said drops. This cooling stage can be carried out by any type of process well known to a person skilled in the art, for example by immersion in a coolant (quenching, cold air, and the like) or by dropping drops onto a moving metal surface cooled by a cooling liquid. Preferentially, this cooling stage is carried out by dropping drops onto a cooling belt composed of a moving metal belt cooled by a water circuit or by dropping drops onto a horizontal plate cooled by a cooling liquid. The cooling of the drops has to be such that said drops have to reach a temperature lower than the melting point of the dianhydrohexitol(s), in particular lower than 63±2° C. for isosorbide, so that the shape of said pellets is definitively stabilized.

The synchronization of the feed/metering unit and of the system for cooling the cooling disks, which takes place during the metering of the drops of melt, provides for the shaping of the pellets. In addition, the apparatus can be equipped with a closed-circuit cooling system in order to prevent any contamination of the product by the water vapors or by the cooling fluid, as well as any contamination of the cooling fluid.

According to a preferred form of the present invention, the pelletizer can be a Rotoform® pelletizer sold by Sandvik. Such a pelletizer is composed of a heated stationary cylindrical body (stator) which comprises a longitudinal feed groove and around which a rotating perforated tube is found. When a series of perforations of the tube passes under the groove of the stator, a small amount of product is released and is dropped in the form of drops onto the steel belt, where they are cooled and solidified. The peripheral speed of the pelletizer is synchronized with the rate of forward progression of the steel belt.

Prior to the pelleting process, the dianhydrohexitol composition is prepared, no matter the way, for example according to the process described in the patent EP 1 287 000; it can be subjected to various processes of purification, concentration, crystallization, and the like, well known to a person skilled in the art. In particular, the dianhydrohexitols can be subjected to at least one treatment with active charcoal and/or at least one ion-exchange means. Furthermore, the dianhydrohexitols can be stabilized beforehand according to the teaching of the patent EP 1 446 373.

The dianhydrohexitol pellets according to the invention comprise between 90% and 100% by weight, preferably between 95% and 100% by weight and more preferably between 97% and 100% by weight on a dry basis of the composition of said dianhydrohexitol pellets.

Said pellets according to the invention additionally comprise less than 2% by weight of anticaking agent, preferably less than 0.5% by weight, more preferably still less than 0.01% by weight and more preferably still less than 0.001% by weight on a dry basis of the composition of said dianhydrohexitol pellets.

The pellets in accordance with the invention are furthermore characterized by their bulk density and their tapped density, and also by their tapping, the values being calculated according to the test A described below, using the Stampf Volumeter STAV 2003 device.

Under these conditions, the pellets in accordance with the invention advantageously exhibit:
- a bulk density of between 0.80 and 1.00 g/ml, preferably of between 0.81 and 0.85 g/ml and more preferably still of between 0.82 and 0.84 g/ml,
- a tapped density of between 0.81 and 1.00 g/ml, preferably of between 0.82 and 0.86 g/ml and more preferably still of between 0.83 and 0.85 g/ml, and
- a tapping at most equal to 2%, preferably between 0.5% and 2% and more preferably still between 0.8% and 1.6%.

The tapped and bulk density and also tapping values of the pellets in accordance with the invention are determined, according to the test A, using the Stampf Volumeter STAV 2003 device, following the method recommended in the directions for use of said Stampf Volumeter. Thus, the test A consists in introducing an amount of product, such that it fills a volume of 250 ml, into a measuring cylinder with a diameter of 35 mm and a height of 335 mm. Whatever the product tested, the product is introduced into said measuring cylinder so as to always fill one and the same volume of 250 ml (volume before tapping). The volume of product (volume after tapping) is subsequently measured after 1250 taps given from the top downward (drop of 3 mm+/−0.2).

The Stampf Volumeter STAV 2003 device thus makes it possible to measure, under standardized and reproducible conditions, the aptitude for tapping of a product by calculating the bulk density, the tapped density and, from these data, the tapping values according to the following formulae:

Bulk density=weight of product introduced into the measuring cylinder(g)/250(ml)

Tapped density=weight of product introduced into the measuring cylinder(g)/$X$(ml)

with $X$=volume(ml) occupied by the product after tapping

Tapping(%)=[(tapped density−bulk density)/bulk density]×100 with tapped density=tapped density after a tapping carried out with 1250 taps given from the top downward (drop of 3.0±0.2 mm).

The dianhydrohexitol pellets in accordance with the invention can also be characterized by their compressibility, evaluated according to the test B described below.

The compression test B consists in introducing a certain weight of product, quantified in grams, into a hollow brass cylinder with an internal diameter of 4.8 cm and a height of 8 cm, placed in a crystallizing dish with a diameter of 95 mm. A piston weighing 1.3 kg, fitting exactly into the hollow brass cylinder, is set down on the product present in said cylinder. Whatever the product tested, the cylinder always comprises substantially the same volume of product (the filling height of the cylinder being substantially the same, set at 5.9±0.2 cm). Immediately after putting the piston in place on the product introduced into the cylinder, the precise height of the whole of the product introduced into the cylinder is measured (height before compression). The piston/product/cylinder/crystallizing dish assembly is subsequently placed in an aluminum bag (22 cm×41 cm) (Z 183407 bag sold by Aldrich). The bag is immediately closed by sealing using an impulse heat sealer (SZ 380 model sold by Joisten & Kettenbaum GmbH & Co, Bergisch Gladbach, Germany) in order to ensure leaktightness with respect to the external atmosphere. The samples thus packaged are placed for 1 week in a ventilated oven, thermostatically controlled at a temperature either of 20° C. or of 40° C. After this period of one week, the bag is opened and the precise height of the whole of the product introduced into the cylinder is measured (height after compression). The compressibility of the product is calculated according to the following formulae:

$D_{before}$=weight of product introduced into the cylinder (g)/$[(\pi \times d^2 \times h_{before})/4]$ with $D_{before}$=density before compression in g/cm$^3$; d=internal diameter of the cylinder (cm)=4.8 cm; $h_{before}$=height of the product in the cylinder before compression (cm); π=pi $D_{after}$=weight of product introduced into the measuring cylinder(g)/$[(\pi \times d^2 \times h_{after})/4]$ with $D_{after}$=density after compression in g/cm$^3$; d=internal diameter of the cylinder (cm)=4.8 cm; $h_{after}$=height of the product in the cylinder after compression (cm)

Compressibility(%)=$[(D_{after}-D_{before})/D_{before}]\times 100$

The pellets in accordance with the invention advantageously exhibit a compressibility, evaluated at 20° C., of less than 5%, preferably of less than 3% and more preferably still of less than 2%. Said pellets in addition advantageously exhibit a compressibility, evaluated at 40° C., of less than 5%, preferably of less than 4.5%.

The pellets in accordance with the invention can also be characterized by their low aptitude for caking. The aptitude for caking is evaluated in particular using the test C described below.

The caking test C, which is similar to that described in the first claim of the patent application EP 1 787 993 A1, consists in introducing 70 g of product into a glass flask with a height of 12 cm and an internal diameter of 6 cm. Said flask, thus filled, is hermetically closed and placed, for 2 or 4 weeks, in a ventilated oven, the internal temperature of which is set at 20° C. or at 40° C. After 2 or 4 weeks, the flask is removed from the oven, opened and then inverted by an angle of 90° and then of 180° along a horizontal axis. A score is assigned to the product according to its form of flow:
- a score of 0 is assigned to the product if it flows completely and immediately when the flask is placed at 90°;
- a score of 1 is assigned to the product if it flows completely within a maximum period of time of 1 minute when the flask is placed at 180°;
- a score of 2 is assigned to the product if it
  does not flow, even after the flask has been placed at 180° for more than one minute, but
  flows after a weight of 300 g has been dropped, from a height of 10 cm, onto the base of the flask placed at 180°;
- a score of 3 is assigned to the product if it does not flow, even after the flask has been placed at 180° for more than one minute and after a weight of 300 g has been dropped, from a height of 10 cm, onto the base of the flask placed at 180°.

The pellets in accordance with the invention advantageously exhibit a score of 1 in the caking test C carried out at 20° C. for 2 or 4 weeks and a score of 1 or 2 in the caking test C carried out at 40° C. for 2 or 4 weeks.

The pellets in accordance with the invention can also exhibit the advantage of being chemically stable during storage. According to the invention, the chemical stability is evaluated, according to the test D, by pHmetry (confirmation of the stability of the pH).

The stability test D consists in evaluating, in a first step, the pH of a sample of product dissolved, at 40% by weight of dry matter, in osmosed water. Subsequently, 50 g of another sample of this same product are introduced into a glass flask and then said flask is hermetically closed and placed in a ventilated oven, thermostatically controlled at a temperature of 50° C. Several flasks, filled with the same product, are placed in the oven. After a predetermined period, all of the sample of product is extracted from the flasks and dissolved, at 40% by weight of dry matter, in osmosed water. The pH measurement is carried out on a pHmeter of Radiometer Analytical PHM 220 brand equipped with a combined Ag/AgCl wire electrode of Mettler Toledo brand, calibrated beforehand using pH 7 and 4 buffer solutions.

The pellets in accordance with the invention advantageously exhibit a pH, evaluated according to the test D, of greater than or equal to 7, preferably of between 7.0 and 8.5, after 6 months of storage in a glass flask placed in a ventilated oven thermostatically controlled at a temperature of 50° C. This pH, of greater than or equal to 7, shows an absence of generation of acidity (synonymous with decomposition of the dianhydrohexitols with formation of formic acid) and shows an excellent stability of the dianhydrohexitol pellets in accordance with the invention.

The pellets in accordance with the invention also exhibit the advantage of rapidly dissolving, their dissolution time being the same as those of the other shaping outcomes known to date. Thus, the pellets in accordance with the invention can be characterized by a dissolution time in water of less than or equal to:
- 12 minutes, preferably 10 minutes, when said pellets are dissolved at 20° C. in a final dry matter in the solution of 50%; and
- 6 minutes, preferably 5 minutes, when said pellets are dissolved at 40° C. in a final dry matter in the solution of 50%.

According to the invention, the dissolution is evaluated according to the test E. Said dissolution test E consists in introducing a test portion of 100 g of product into a 250 ml beaker containing 100 ml of distilled water preheated to 20° C.±2° C. or to 40° C.±2° C. The product/distilled water combination is stirred using a magnetic bar (reference No. ECN 442-4510/VWR). The time which has passed between the introduction of the test portion into the beaker and the complete dissolution of the test portion in the water is then determined. The experiment is carried out 3 times for each sample. According to the present invention, the dissolution time of the sample corresponds to the mean of the results of the three experiments.

The dianhydrohexitol pellets in accordance with the invention also exhibit the advantage of being able to rapidly melt, their melting time being of the same order of magnitude as those of the other shaping outcomes known to date. Thus, the pellets in accordance with the invention can be characterized by a melting time of less than 25 minutes, preferably 22 minutes, when said pellets are heated to 80° C.

According to the invention, the melting time is evaluated according to the test F. Said melting test F consists in introducing a test portion of 100 g of product into a 250 ml beaker heated beforehand to 80° C.±2° C. The test portion is stirred using a magnetic bar (reference No. ECN 442-4510/VWR). The time which has passed between the introduction of the test portion into the beaker and the complete melting of the test portion is then determined. The experiment is carried out 3 times for each sample. According to the present invention, the melting time of the sample corresponds to the mean of the results of the three experiments.

The pellets in accordance with the invention are also advantageously characterized in that at least 90% by weight, preferably 95% by weight and more preferably still 94% by weight of the pellets exhibit a particle size on sieves of greater than or equal to 2000 μm, preferably of between 2000 μm and 20 000 μm. According to the invention, the particle size on sieves of the pellets is evaluated according to the test G described below.

Said test G is carried out using the VS 1000 laboratory siever sold by Retsch, according to the method recommended in the directions for use of said siever. According to the test G, said siever is equipped with a sieving tower composed of 7 sieves with a diameter of 20 cm, the mesh sizes of which are respectively 20 000 μm, 5000 μm, 2000 μm, 1400 μm, 1000 μm, 500 μm and 355 μm (the sieves are placed from the top downward, from the widest mesh size down to the narrowest mesh size). Briefly, the test G consists in introducing a test portion of 200 g of product at the top of the sieving tower and in starting the siever in continuous mode, at a vibrational amplitude of 50%, for 10 minutes. After sieving for 10 minutes, the siever is halted and the amount of product retained on each of the sieves is quantified by weighing.

The pellets according to the invention preferably exhibit a moisture content, evaluated by the Karl Fischer method, of less than 1% by weight, preferably of less than 0.5% by weight and more preferably still of less than 0.3% by weight of the dianhydrohexitol composition of said pellets.

The pellets according to the invention or capable of being obtained by the process according to the invention make it possible to produce specific compositions suited to fields as diversified as nutraceuticals, pharmaceuticals, cosmetics, chemistry, construction materials, paper/board or polymers. Thus, the present invention additionally relates to the use of the pellets according to the invention or obtained by the process according to the invention in the manufacture of derivatives of dianhydrohexitols and of polymers comprising at least one dianhydrohexitol or one derivative of the latter.

An even better understanding of the invention will be obtained with the help of the following examples, which are not meant to be limiting and report only certain embodiments and certain properties which are advantageous of the pellets in accordance with the invention.

EXAMPLES

In the examples 2 to 6 below:
- the term "pellets V1, V2 and V3" is understood to mean isosorbide pellets in accordance with the invention with a thickness of 2 mm, the greatest length (diameter) of which are respectively 4 mm, 5 mm and 7 mm, obtained according to the pelleting process described in detail in example 1;
- the term "flakes" is understood to mean isosorbide flakes obtained by crystallization on a cooled rotating cylinder, feeding being carried out by dipping in a vat containing the molten isosorbide;
- the term "bulk crystals" is understood to mean isosorbide crystals obtained by crystallization from a solvent of alcohol type, followed by filtering off and drying under vacuum in a filter-dryer of said crystals obtained;
- the term "355-1400 crystals" is understood to mean crystals resulting from a 355-1400 μm particle size fraction produced from the "bulk crystals" described above. The particle size fraction is produced using the VS 1000 laboratory siever sold by Retsch, the method recommended in the directions for use of said siever being followed. Said siever is equipped, for producing the fraction, with a sieving tower composed of 2 sieves with a diameter of 20 cm, the mesh sizes of which are respectively 355 µm and 1400 µm (the sieves are placed from the top downward, from the widest mesh size down to the narrowest mesh size).

Example 1

Preparation of Isosorbide Pellets in Accordance with the Invention

Isosorbide with a purity of 99.8% and comprising 0.2% of water is introduced in the form of flakes into a heated and stirred cylindrical vessel. When the product has been completely melted, it is maintained at a temperature of 65° C.±2° C. and pelleting is carried out using the Rotoform® 3000 pelletizer sold by Sandvik.

Operating Parameters:
Feed temperature: 65° C.±2° C.
Speed of the belt: 9.5 m/min
Speed of the Rotoform®: 11 m/min
Belt width: 600 mm
Cold belt length: 7.5 m
Total length of the belt: 10 m
Cooling water for the belt: filtered decarbonated water at 20° C. with a flow rate of 5 m³/h
Pellet production rate: 360 kg/h The choice of the perforation diameter of the feed tube makes it possible to obtain pellets with different diameters.

The following pellets are obtained by applying the operating parameters described above with feed tubes with appropriate perforation diameters:
pellets V1: diameter 4 mm and thickness 2 mm
pellets V2: diameter 5 mm and thickness 2 mm
pellets V3: diameter 7 mm and thickness 2 mm Likewise, the same procedure as above is followed, taking as starting material isosorbide with a purity of 97% in the form of flakes. The following pellets are thus obtained by applying the operating parameters described above with feed tubes with appropriate perforation diameters:
pellets V4: diameter 4 mm and thickness 2 mm
pellets V5: diameter 5 mm and thickness 2 mm
pellets V6: diameter 7 mm and thickness 2 mm Example 2

Comparison of the Behavior of the Isosorbide Compositions in Accordance with the Invention and of the Isosorbide Compositions in the Form of Flakes or Crystals During Tapping and Compression Tests 2.1 Tapping Test The bulk density, the tapped density and the tapping of different isosorbide shaping outcomes are evaluated according to the test A. These parameters are in particular compared for isosorbide pellets with different diameters (V1, V2 and V3) in accordance with the invention, isosorbide flakes and isosorbide crystals (bulk crystals or crystals resulting from a 355-1400 µm fraction).

The results of this evaluation are presented in table 1.

TABLE 1

Results of the tapping tests carried out on different isosorbide shaping outcomes

| Form | Volume after tapping (ml) | Weight (g) | Density before tapping (g/ml) | Density after tapping (g/ml) | Tapping (%) |
|---|---|---|---|---|---|
| Pellets V1 | 248 | 207.7 | 0.83 | 0.84 | 0.8 |
| Pellets V2 | 246 | 208.9 | 0.84 | 0.85 | 1.6 |
| Pellets V3 | 248 | 205.3 | 0.82 | 0.83 | 0.9 |
| Flakes | 239 | 185.9 | 0.74 | 0.78 | 4.6 |
| Bulk crystals | 230 | 168.1 | 0.67 | 0.73 | 8.8 |
| Crystals (355-1400 µm) | 230 | 166.7 | 0.67 | 0.73 | 8.7 |

The pellets in accordance with the invention exhibit a bulk density and a tapped density which are far superior to those of the products existing on the market (flakes and crystals). In addition, said pellets exhibit a tapping which is very markedly lower than that of the flakes and crystals.

In comparison with the other forms of shaping outcome, the isosorbide pellets are thus more suitable for being transported in large volume since they settle down less and are thus less susceptible to caking and since they exhibit, despite this, a greater density, both tapped and bulk.

2.2 Compression Test

The density before compression ($D_{before}$), the density after compression ($D_{after}$) and the compressibility of different isosorbide shaping outcomes are evaluated according to the test B. These parameters are in particular compared for isosorbide pellets V1, V2 and V3 in accordance with the invention, isosorbide flakes and isosorbide crystals (bulk crystals or crystals resulting from a 355-1400 µm fraction).

The results of this evaluation are presented in table 2.

TABLE 2

Results of the compression tests carried out on different isosorbide shaping outcomes Oven thermostatically controlled at 20° C.:

| Form | Height before (cm) | Height after (cm) | Weight before (g) | $D_{before}$ (g/cm³) | $D_{after}$ (g/cm³) | Compressibility (%) |
|---|---|---|---|---|---|---|
| Pellets V1 | 5.8 | 5.7 | 90.5 | 0.86 | 0.88 | 2 |
| Pellets V2 | 5.7 | 5.7 | 90.5 | 0.88 | 0.88 | 0 |
| Pellets V3 | 5.9 | 5.9 | 91.1 | 0.85 | 0.85 | 0 |
| Flakes | 6.1 | 5.7 | 83.6 | 0.76 | 0.81 | 7 |
| Bulk crystals | 5.9 | 5.3 | 78.4 | 0.73 | 0.82 | 11 |
| Crystals, 355-1400 | 5.9 | 5.3 | 78.6 | 0.74 | 0.82 | 11 |

Oven thermostatically controlled at 40° C.:

| Form | Height (cm) before tapping | Height (cm) after tapping | Weight (g) before tapping | $D_{before}$ (g/cm³) | $D_{after}$ (g/cm³) | Compressibility (%) |
|---|---|---|---|---|---|---|
| Pellets V1 | 5.8 | 5.6 | 90.6 | 0.86 | 0.89 | 4 |
| Pellets V2 | 5.7 | 5.5 | 90.6 | 0.88 | 0.91 | 4 |
| Pellets V3 | 6.0 | 5.8 | 92.4 | 0.85 | 0.88 | 4 |
| Flakes | 5.9 | 5.5 | 83.7 | 0.78 | 0.84 | 7 |
| Bulk crystals | 5.8 | 5.1 | 77.4 | 0.74 | 0.84 | 14 |

TABLE 2-continued

Results of the compression tests carried out
on different isosorbide shaping outcomes

| | | | | | | |
|---|---|---|---|---|---|---|
| Crystals, 355-1400 | 5.8 | 5.1 | 78.5 | 0.75 | 0.85 | 14 |

The pellets in accordance with the invention exhibit a density before and after compression (respectively $D_{before}$ and $D_{after}$) which are far superior to those of the products existing on the market (flakes and crystals). In addition, said pellets exhibit a compressibility which is markedly lower than that of the flakes and crystals.

In comparison with the other forms of shaping outcome, the isosorbide pellets are thus more suited to being transported in large volume since they are less compressible.

Example 3

Comparison of the Behavior of the Isosorbide Compositions in Accordance with the Invention and of the Isosorbide Compositions in the Form of Flakes or Crystals During Caking Tests The aptitude for caking of isosorbide pellets in accordance with the invention, of isosorbide flakes and of isosorbide crystals was evaluated according to the caking test C as described above.

The results of this evaluation are presented in table 3.

TABLE 3

Results of the caking tests in a ventilated oven thermostatically
controlled at 20° C. or at 40° C. carried
out on different isosorbide shaping outcomes

| Time (weeks) | Pellets | | | | Crystals | |
|---|---|---|---|---|---|---|
| | V1 | V2 | V3 | Bulk | 355-1400 μm | Flakes |
| Oven thermostatically controlled at 20° C.: | | | | | | |
| 2 | 1 | 1 | 1 | 2 | 2 | 1 |
| 4 | 1 | 1 | 1 | 2 | 2 | 1 |
| Oven thermostatically controlled at 40° C.: | | | | | | |
| 2 | 2 | 1 | 1 | 2 | 2 | 2 |
| 4 | 2 | 2 | 2 | 3 | 3 | 2 |

Scores: 0=product flowing completely and immediately when the flask is placed at 90°; 1=product flowing completely within a maximum period of time of 1 minute when the flask is placed at 180°; 2=product not flowing, even after the flask has been placed at 180° for more than one minute, but flowing after a weight of 300 g has been dropped, from a height of 10 cm, onto the base of the flask placed at 180°; 3=product not flowing, even after the flask has been placed at 180° for more than one minute and after a weight of 300 g has been dropped, from a height of 10 cm, onto the base of the flask placed at 180°.

The isosorbide pellets in accordance with the invention exhibit a score of 1 in the caking test C carried out at 20° C. for 2 or 4 weeks and a score of 1 or 2 in the caking test C carried out at 40° C. for 2 or 4 weeks.

Example 4

Analysis of the Chemical Stability of Isosorbide Pellets in Accordance with the Invention The stability on storage of pellets obtained according to example 1 was evaluated according to the test D as described above.

The results of this evaluation are presented in table 4.

TABLE 4

Results of the stability tests D carried out on the
pellets in accordance with the invention

| Storage time | Pellets V1 | Pellets V2 | Pellets V3 |
|---|---|---|---|
| 0 day | 7.6 | 7.6 | 7.6 |
| 15 days | 7.9 | 7.8 | 8.0 |
| 1 month | 8.0 | 7.6 | 8.0 |
| 2 months | 8.1 | 7.8 | 7.9 |
| 3 months | 8.0 | 7.6 | 8.1 |
| 4 months | 7.9 | 7.4 | 8.0 |
| 6 months | 8.1 | 7.8 | 8.1 |

The pH values of the different pellets V1, V2 and V3 remain stable, even after storing at 50° C. for 6 months, which shows an absence of generation of acidity (synonymous with decomposition of the isosorbide with formation of formic acid) and thus an excellent stability of the isosorbide pellets in accordance with the invention.

Example 5

Evaluation of the Dissolution and Melting Times of Isosorbide Pellets in Accordance with the Invention and of the Isosorbide Compositions in the Form of Flakes or Crystals The dissolution time and the melting time of different isosorbide shaping outcomes were evaluated according to the tests E and F respectively.

The results of this evaluation are presented in tables 5 and 6 respectively.

TABLE 5

Results of the dissolution tests E carried out on
different isosorbide shaping outcomes

| Shaping outcome (100 g) | Dissolution time in water (min) | |
|---|---|---|
| | 20° C. | 40° C. |
| Flakes | 5.7 | 4.1 |
| Bulk crystals | 8.9 | 3.6 |
| Pellets V1 | 6.6 | 3.4 |
| Pellets V2 | 7.8 | 3.6 |
| Pellets V3 | 9.9 | 4.9 |

TABLE 6

Results of the melting tests F carried out on
different isosorbide shaping outcomes

| Shaping outcome | Melting time (min) |
|---|---|
| Flakes | 15.9 |
| Bulk crystals | 17.8 |
| Pellets V1 | 16.2 |

TABLE 6-continued

Results of the melting tests F carried out on different isosorbide shaping outcomes

| Shaping outcome | Melting time (min) |
|---|---|
| Pellets V2 | 20.4 |
| Pellets V3 | 22.8 |

The isosorbide pellets in accordance with the invention exhibit a dissolution time which is substantially the same as those of the other shaping outcomes known to date.

In addition, said pellets exhibit a melting time of the same order of magnitude as those of the other shaping outcomes known to date.

Example 6

Particle Size Analysis of the Isosorbide Compositions in Accordance with the Invention and of the Isosorbide Compositions in the Form of Flakes or Crystals The particle size on sieves of different isosorbide shaping outcomes was evaluated according to the test G. The results of this evaluation are presented in table 7.

TABLE 7

Particle size according to the test G carried out on different isosorbide shaping outcomes (% of oversize by weight)

| Shaping outcome | Particle size on sieves (µm) | | | | | | | |
|---|---|---|---|---|---|---|---|---|
| | >20 000 | 5000 to 20 000 | 2000 to 5000 | 1400 to 2000 | 1000 to 1400 | 500 to 1000 | 355 to 500 | <355 |
| Pellets V1 | 0 | 51.2 | 46.2 | 1.4 | 1.2 | 0.1 | 0 | 0 |
| Pellets V2 | 0 | 64.0 | 31.9 | 2.5 | 1.4 | 0.3 | 0 | 0 |
| Pellets V3 | 0 | 63.0 | 31.1 | 3.8 | 1.1 | 0.8 | 0.2 | 0 |
| Flakes | 0 | 20.3 | 52.1 | 14.6 | 10.5 | 2.6 | 0 | 0 |
| Bulk crystals | 0 | 0.9 | 6.2 | 9.1 | 71.2 | 12.6 | 0 | 0 |
| Crystals, 355-1400 µm | 0 | 0.1 | 0.3 | 8.4 | 87.7 | 3.3 | 0.2 | 0 |

The isosorbide pellets in accordance with the invention are also characterized in that at least 90% by weight, preferably 94% by weight, of the pellets exhibit a particle size on sieves of greater than 2000 µm, preferably of between 2000 µm and 20 000 µm.

The invention claimed is:

1. A composition of high-fluidity and non-caking dianhydrohexitol pellets comprising between 90% and 100% by weight of dianhydrohexitols on a dry basis, wherein at least 90% by weight of said pellets exhibit a particle size on sieves of greater than or equal to 2000 µm and wherein said pellets are selected from the group consisting of tablets, pebbles, granules, bars, beads, other shapes obtained by pelleting, and mixtures thereof.

2. The composition of dianhydrohexitol pellets as claimed in claim 1, wherein said pellets are of round, oval, square, rectangular, octagonal or polygonal shape.

3. The composition of dianhydrohexitol pellets as claimed in claim 1, wherein said pellets are dome-shaped.

4. The composition of dianhydrohexitol pellets as claimed in claim 1, comprising less than 2% by weight of anticaking agent on a dry basis.

5. The composition of dianhydrohexitol pellets as claimed in claim 1, wherein said dianhydrohexitols are selected from the group consisting of isosorbide, isomannide, isoidide and the mixtures thereof.

6. The composition of dianhydrohexitol pellets as claimed in claim 1, said dianhydrohexitol pellets exhibiting:
a bulk density of between 0.80 and 1.00 g/ml,
a tapped density, evaluated according to a test A, of between 0.81 and 1.00 g/ml.

7. The composition of dianhydrohexitol pellets as claimed in claim 1, said dianhydrohexitol pellets exhibiting a tapping, evaluated according to the test A, at most equal to 2%.

8. The composition of dianhydrohexitol pellets as claimed in claim 1, said dianhydrohexitol pellets exhibiting a compressibility, evaluated according to a test B carried out at 20° C., of less than 5%.

9. The composition of dianhydrohexitol pellets as claimed in claim 1, said dianhydrohexitol pellets exhibiting a score of 1 in a caking test C carried out at 20° C. for 2 or 4 weeks and a score of 1 or 2 in the caking test C carried out at 40° C. for 2 or 4 weeks.

10. The composition of dianhydrohexitol pellets as claimed in claim 1, said dianhydrohexitol pellets exhibiting a pH of greater than or equal to 7 after 6 months of storage in a ventilated oven thermostatically controlled at a temperature of 50° C.

11. The composition of dianhydrohexitol pellets as claimed in claim 1, wherein at least 95% by weight of the pellets exhibit a particle size on sieves of greater than or equal to 2000 µm.

12. The composition of dianhydrohexitol pellets as claimed in claim 1, said dianhydrohexitol pellets exhibiting a moisture content of less than 1% by weight.

13. The composition of dianhydrohexitol pellets as claimed in claim 1, said dianhydrohexitol pellets exhibiting a flat face and a convex face.

* * * * *